United States Patent [19]

Burke et al.

[11] Patent Number: 4,783,546

[45] Date of Patent: Nov. 8, 1988

[54] PREPARATION OF 4-PENTENENITRILE BY ISOMERIZATION

[75] Inventors: Patrick M. Burke; Norman Herron; Francis J. Waller, all of Wilmington, Del.

[73] Assignee: E. I. Du Pont de Nemours and Company, Wilmington, Del.

[21] Appl. No.: 57,433

[22] Filed: Jun. 2, 1987

[51] Int. Cl.$^4$ .......................................... C07C 121/30
[52] U.S. Cl. ................................................ 558/355
[58] Field of Search ........................................ 558/355

[56] References Cited

U.S. PATENT DOCUMENTS

| | | | |
|---|---|---|---|
| 3,526,654 | 9/1970 | Hildebrand et al. | 558/355 |
| 3,542,847 | 11/1970 | Drinkard, Jr. et al. | 558/355 |
| 3,676,481 | 7/1972 | Chia | 558/355 |
| 3,852,325 | 12/1974 | King | 558/355 |
| 4,022,847 | 5/1977 | McClure | 585/462 X |
| 4,038,213 | 7/1977 | McClure et al. | 585/332 X |
| 4,529,815 | 7/1985 | Schneider et al. | 560/205 |

OTHER PUBLICATIONS

Translation of Fed. Rep. of Germany "Preliminary Published Application" DE 3521 380A1, published 12-18-86, (13 pp. total).

Translation of Fed. Rep. of Germany "Preliminary Published Application" DE 3521 381A1, published 12-18-86, (16 pp. total).

*Primary Examiner*—Joseph Paul Brust

[57] ABSTRACT

Isomerization by contacting 3-pentenenitrile with a heterogeneous catalyst, preferably promoted with at least 1 group 8 noble metal, to form 4-pentenenitrile.

2 Claims, No Drawings

PREPARATION OF 4-PENTENENITRILE BY ISOMERIZATION

FIELD OF THE INVENTION

This invention relates to a process for the selective isomerization of 3-pentenenitrile to form 4-pentenenitrile by the use of a particular class of catalysts that are not dissolved in the reaction mixture. The process requires contacting the 3-pentenenitrile with the catalyst at elevated temperatures.

BACKGROUND OF THE INVENTION

3-Pentenenitrile (3PN) is produced commercially by the hydrocyanation of butadiene in the presence of nickel catalysts:

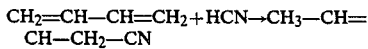

3PN is a precursor for the production of the nylon intermediates, adiponitrile (by further hydrocyanation), or adipic acid and caprolactam (by carbonylation to 5-cyanovaleric acid). To form these intermediates, 3PN must first be converted to the terminal olefinic isomer, 4-pentenenitrile (4PN):

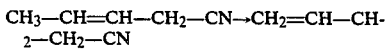

Some hydrocyanation catalysts are also effective for this isomerization, allowing the selective production of adiponitrile commercially by hydrocyanation of 3PN:

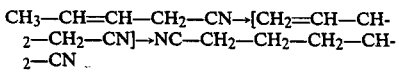

However, carbonylation catalysts are, in general, relatively poor isomerization catalysts and they are also less selective in the carbonylation of internal vs terminal double bonds. These factors lead to lower yields of 5-cyanovaleric acid and its esters in the carbonylation of 3PN. In contrast, much higher selectivity to 5-cyanovaleric acid can be obtained by carbonylation of 4PN:

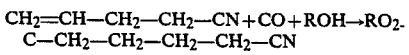

The present invention is concerned with the isomerization of 3-pentenenitrile to 4-pentenenitrile.

U.S. Pat. No. 3,542,847 to Drinkard et al. discloses the isomerization of 3-pentenenitrile to 4-pentenenitrile by the use of homogeneous palladium or platinum catalysts having a valence of plus 2 or less; and when the platinum or palladium is a zero valent state, an acid is preferably also present.

It is also known from U.S. Pat. No. 4,529,815 to prepare 4-pentenoates using an acidic ion-exchange resin or zeolite containing a noble metal of group 8 of the periodic table as the catalyst.

Perfluorinated ion-exchange resins have been previously employed as isomerization catalysts—see, for example, U.S. Pat. Nos. 4,022,847 and 4,038,213 to McClure and McClure et al. which disclose the isomerization of alkanes.

SUMMARY OF THE INVENTION

The present invention is a process for the preparation of 4-pentenenitrile by the isomerization of 3-pentenenitrile by contacting at elevated temperature the 3-pentenenitrile with a catalyst selected from the group consisting of acidic ion-exchange resins promoted with at least one group 8 noble metal, acid zeolites promoted with at least one group 8 noble metal, amorphous silica aluminates promoted with at least one group 8 noble metal, activated carbon promoted with at least one group 8 noble metal, and perfluorinated acid ion-exchange resins. The acidic ion-exchange resin promoted with a group 8 noble metal may be a perfluorinated acid ion-exchange resin.

In a preferred embodiment the heterogeneous catalyst is selected from a perfluorinated ion-exchange resin in the acid form containing at least one group 8 noble metal in an oxidation state of at least +2 as a promoter or an acidic Y-zeolite containing at least one group 8 noble metal of the periodic table. The preferred noble metals are platinum, rhodium and palladium. It is preferable to have the noble metal present in the amount of 0.1% to 4% by weight of the catalyst.

DETAILED DESCRIPTION

The isomerization process of the present invention involves the use of a heterogeneous catalyst. Suitable catalysts have already been broadly described above. When the catalyst is an acidic ion-exchange resin promoted with a group 8 noble metal, the acidic ion-exchange resin may be, for example, a styrene/divinyl benzene ion-exchange resin, or a perfluorinated acid ion-exchange polymer. A perfluorinated acid ion-exchange polymer catalyst is prepared from a suitable perfluorinated acid ion-exchange polymer (PFIEP[SO$_3$H]), or a blend of perfluorinated sulfonic acid and perfluorinated carboxylic acid polymers (PFIEP[SO$_3$H]/PFIEP[CO$_2$H]). Most preferred perfluorinated sulfonic acid polymers have a number average molecular weight of at least about 5000. Preferably, the PFIEP contains a sufficient number of sulfonic acid groups to give an equivalent weight of from about 500 to about 2000, and most preferably from about 700 to about 1500. The equivalent weight, E.W., is determined by the formula:

E.W.=M.W./number of acid groups, where M.W. is the molecular weight of the perfluorocarbon polymer.

Although the polymer backbone will largely comprise perfluorinated carbon atoms, it is not necessary that all other atoms be excluded. For example, ether oxygen may be present in the backbone or in the side chains of the polymer. Other atoms or groups such as hydrogen, chlorine and carboxyl groups may be present in limited amounts without significantly affecting the stability or operability of the polymer under the process conditions. It is preferred that the polymer contain no greater than about 5 weight percent total of such other atoms or groups.

The perfluorinated acid ion-exchange polymer may be a blend of two or more ion-exchange polymers. The preparation of blends of perfluorinated sulfonic acid and perfluorinated carboxylic acid polymers is disclosed in U.S. Pat. No. 4,176,215, the disclosure of which is incorporated herein by reference. Preferred blends of perfluorinated sulfonic acid and perfluorinated carboxylic acid polymers include blends of tetrafluoroethylene copolymers with methylperfluoro-5-methyl-4,7-dioxanon-8-eneoate and tetrafluoroethylene copolymers with perfluoro(3,6-dioxo-4-methyl-7-octene) sulfonyl fluoride. Most preferred blends have an ion-exchange capacity of at least 0.7 meq/g. Preferably, the weight ratio of sulfonic acid polymer to carboxylic acid polymer in the blend is from about 1:1 to about 10:1.

The perfluorinated acid ion-exchange polymer is ground to small particles—usually 20 to 200 mesh size and employed as catalyst, but improved results are obtained if the perfluorinated acid ion-exchange polymer is subjected to an exchange with a salt of a noble metal of group 8 of the periodic table whereby an amount by weight of the catalyst of between about 0.1 to 4% of the noble metal is incorporated into the perfluorinated acid ion-exchange resin. The noble metal is preferably present in the oxidation state of at least +2. The noble metal acts to promote the reaction.

Suitable hydrocarbon sulfonic acid ion-exchange polymers are commercially available under such trademarks as Dowex resins and Amberlyst 15 resins.

Another suitable catalyst for this isomerization process is noble metal of group 8 of the periodic table in a finely divided form supported on activated carbon. Suitable catalysts are commercially available, e.g., 1 to 10% palladium or 1 to 10% platinum on activated carbon catalysts are available from Aldrich Chemical Company Inc., and 10% palladium on powdered charcoal is available from Matheson Coleman and Bell.

Another suitable catalyst is acidic zeolite promoted with at least one group 8 noble metal. Zeolites are crystalline aluminosilicate compounds. Zeolites occur in nature, and also are synthesized. See Kirk-Othmer: Encyclopedia of Chemical Technology Vol. 15, page 638 through 650, John Wiley & Sons, NY (1981). Commercially available zeolites such as the Y-zeolite sold by Union Carbide Company are satisfactory synthetic zeolites useful in the process of the present invention.

Amorphous silica aluminates are also satisfactory catalysts for the isomerization reaction of the present invention. Such materials can be purchased commercially as Davison Catalyst Supports (from Grace-Davison Chemical Co.).

The isomerization process of this invention may be carried out at temperatures between about 50° C. and 150° C. and at pressures between about 0.01 and 50 atmospheres with a preferred pressure range of between about 0.1 and 5 atmospheres. The optimum operating conditions will depend upon the particular catalyst employed.

EXAMPLES

EXAMPLE 1:

Pd/HY Zeolite Catalyst (a) Catalyst Preparation

To a slurry of 5 g of the NH4Y (LZY-82, Union Carbide) Zeolite in 1000 ml water was added 0.40 g palladium tetramine nitrate. The slurry was stirred for 4 hours at ambient temperature. The Pd-Zeolite was filtered, washed with 1 liter water and suction dried. The solid was dried by heating to 100° C. in flowing oxygen over 1 hour and holding at 100° C. for 30 minutes. It was then calcined by heating at 500° C. in flowing oxygen for 2 hours and then holding at 500° C. for an additional 1 hour in vacuum. It was cooled in vacuum and maintained in an anhydrous atmosphere before use.

Analysis of the solid showed 2.84 wt % Pd.

(b) 3PN to 4PN Isomerization

Crude 3-pentenenitrile, 3PN, was distilled under nitrogen to remove impurities. Gas chromatographic analysis of this product showed the following isomer distribution:

| | |
|---|---|
| trans 3PN | 93.6 |
| cis 3PN | 3.1 |
| trans 2PN | 1.4 |
| cis 2PN | 0.3 |
| 4PN | 1.5 |

4.0 g of the above mixture was heated to reflux (about 140° C.) under nitrogen. To this was added 0.4 g of the 2.84% Palladium/Zeolite catalyst. Samples were taken at intervals and diluted with methanol to quench the reaction. Samples were then analyzed by capillary gas chromatography to determine isomer distribution. No other 3PN byproducts were observed.

The following isomer distributions as a function of time were obtained:

| Time (Min) | * C2PN | ** T2PN | *** 4PN | **** T3PN | ***** C3PN | Δ4PN/ 2PN |
|---|---|---|---|---|---|---|
| 0 | 0.31 | 1.42 | 1.50 | 93.65 | 3.12 | — |
| 1 | 0.99 | 1.17 | 9.34 | 77.15 | 11.35 | 18.2 |
| 5 | 0.94 | 1.18 | 10.90 | 73.70 | 13.28 | 24.1 |
| 30 | 1.08 | 1.33 | 10.09 | 74.76 | 12.74 | 12.6 |

*Cis 2-pentenenitrile
**Trans 2-pentenenitrile
***4-pentenenitrile
****Trans 3-pentenenitrile
*****Cis 3-pentenenitrile The Δ4PN/2PN ratio shows that 4PN is produced 12 to 24 times faster than 2PN under these conditions. This ratio, selectivity, is the number of moles of 4PN formed, divided by the number of moles of 2PN formed during the isomerization reaction. In making this latter calculation, the number of moles of 2PN (cis+trans isomers) present in the starting mixture containing 3PN is not considered.

EXAMPLE 2

A. Catalyst Preparation

The H+ form of a commercially available perfluorinated ion-exchange polymer, PFIEP, having an equivalent weight of about 1000 and a particle size of less than 100 mesh (6.0 g; 6 Meq H+) was stirred in a solution of PtCl2 (0.2 g; 0.75 mmole) in a mixture of 50 ml acetonitrile and 100 ml distilled water. The mixture was maintained at 80° C. for 2 hours. The resin was filtered, washed with 100 ml distilled water and dried in a vacuum oven at 100° under N2 for 3 hours. The dried resin weighed 6.24 g. Analysis showed 1.56% Pt.

B. Isomerization

The experiment in Example 1B was repeated except that the Pd/Zeolite was replaced with 0.40 g 1.56% Pt/PFIEP catalyst. The following Table shows the amounts of 4PN and 2PN (Cis+trans isomers) at the times indicated:

| Time (Min) | 2PN | 4PN | * Δ4PN/ 2PN |
|---|---|---|---|
| 0 | 1.73 | 1.50 | — |
| 1 | 1 95 | 7.23 | 26.0 |
| 5 | 1.75 | 8.20 | 33.5 |
| 30 | 1.86 | 8.27 | 52.0 |

*This ratio is the selectivity of the catalyst. See explanation in Example 1.

The data shows that 4PN is formed much more rapidly than 2PN.

EXAMPLE 3

10% Pd/Activated Carbon

The experiment in example 1B was repeated except that the zeolite was replaced with 0.1 g of a commercially available catalyst consisting of 10% palladium metal on activated carbon. Capillary gas chromatographic analysis as a function of time gave the following results.

| Time (Min) | 2PN | 4PN | Δ4PN/ 2PN* |
|---|---|---|---|
| 0 | 1.73 | 1.50 | — |
| 1 | 2.08 | 2.81 | 3.7 |
| 30 | 2.17 | 2.91 | 3.2 |

*Selectivity - see explanation in Example 1.

EXAMPLE 4

A. Catalyst Preparation: 0.55% Pd/HCl treated amorphous silica-aluminate (13% $Al_2O_3$)

Commercial (Davison) Silica aluminate (10 micron powder) containing 13% alumina was treated with HCl and palladium tetraamine chloride as follows:

5 g of amorphous silica-aluminate containing 13 wt % alumina were slurried into 1000 cc water and acidified to pH 1.0 with hydrochloric acid. The slurry was stirred for 30 minutes then filtered and washed with 1000 cc distilled water. The solid was slurried into 1000 cc fresh distilled water and 0.05 g palladium tetraamine chloride was added. The slurry was stirred for 4 hours then filtered and washed with 1000 cc distilled water. The suction-dried solid was loaded into a horizontal tube furnace quartz tube and oxygen gas was flowed over it while the temperature was ramped up to 100° C. at 2° C./min. The sample was held at 100° C. in flowing oxygen for 30 mins and then temperature was rapidly increased to 400° C. for a further 2 hours in flowing oxygen (~50 cc/min). The oxygen flow was terminated and the tube evacuated at 400° C. for a further 1 hour. The sample was cooled under vacuum then sealed and taken into an inert (nitrogen) atmosphere dry box where it was divided into 1 g lots in separate screw-capped vials.

Chemical analyses showed about 0.55 wt % Pd.

B. Catalytic conversion of 3PN to 4PN

A 10 g sample of 3PN containing 97.2% trans 3PN, 2.0% cis 3PN and 0.8% 4PN (no 2PN) was heated to 140° under $N_2$. To this was added 1.0 g of the Pd/Silica-aluminate catalyst of part A. Samples were taken at intervals and analyzed by capillary gas chromatography. The following results were obtained:

| Time (Min) | 2PN | 4PN | Δ4PN/ 2PN* |
|---|---|---|---|
| 0 | 0 | 0.8 | — |
| 1 | 0.4 | 3.1 | 5.7 |
| 5 | 0.4 | 4.6 | 9.5 |
| 30 | 1.3 | 9.3 | 6.5 |

*Selectivity - see explanation in Example 1.

EXAMPLE 5

The experiment in Example 4B was repeated except that the catalyst was an amorphous silica-aluminate containing 25% $Al_2O_3$ and 0.6% Pd.

The following results were obtained:

| Time (Min) | 2PN | 4PN | Δ4PN/ 2PN* |
|---|---|---|---|
| 0 | 0 | 0.8 | — |
| 1 | 0.5 | 2.6 | 3.6 |
| 5 | 0.7 | 3.8 | 4.3 |
| 30 | 1.5 | 6.4 | 3.7 |

*Selectivity - see explanation in Example 1.

EXAMPLE 6

The experiment in Example 4B was repeated except that the catalyst was an acid exchanged perfluorinated ion-exchange polymer, PFIEP, in the sulfonic acid form (more fully described in Example 2) containing 0.91% Pt. Analysis showed the following isomer distributions:

| Time (Min) | 2PN | 4PN | Δ4PN/ 2PN* |
|---|---|---|---|
| 0 | 0 | 0.8 | — |
| 30 | 0.4 | 3.5 | 6.7 |
| 60 | 0.3 | 5.5 | 15.7 |

*Selectivity - see explanation in Example 1.

EXAMPLE 7

Miscellaneous Group 8 Noble Metal Exchanged Acidic Ion-Exchange Resins

The experiment in Example 4B was repeated except that different catalysts (1.0 g per 10 g T3PN) were used. Analysis after 30 minutes gave the following results:

| Catalyst | 2PN | 4PN | Δ4PN/2PN*** |
|---|---|---|---|
| $Rh^{+3}$ on PFIEP[$SO_3H$] (0.85% Rh) | 0.3 | 1.6 | 2.7 |
| *PS—DVB/$H^+$, $Pd^{+2}$ (1.3% Pd) | 0.5 | 2.8 | 4.0 |
| *PS—DVB/$H^+$, $Pt^{+2}$ (2.8% Pt) | 0.3 | 1.7 | 3.0 |
| *PS—DVB/$H^+$, $Rh^{+3}$ (3.98% Rh) | 0.4 | 2.5 | 4.2 |
| **$Pt^{+2}$ on PFIEP[$SO_3H$]/ PFIEP[$CO_2H$] (0.7% Pt) | 0.4 | 1.9 | 2.7 |

*Polystyrene-divinyl benzene ion-exchange resin (commercially available as "Amberlyst-15" Rohm & Haas).
**This blend contained about 70% PFIEP in sulfonic acid form, and about 30% in carboxylic acid form.
***Selectivity - see explanation in Example 1.

EXAMPLE 8

Prefluorinated Ion-Exchange Resin—without promoter

A. To 10.0 g trans 3PN at 140° was added 5 g PFIEP[$SO_3H$] (sulfonic acid form). Samples were taken at intervals and analyzed for PN isomers. The following results were obtained:

| Time (Min) | 2PN | 4PN | Δ4PN/2PN* |
|---|---|---|---|
| 0 | 0 | 0.8 | — |
| 5 | 0 | 1.3 | — |
| 30 | 0 | 2.2 | — |
| 60 | 0.5 | 2.4 | 4.8 |

*Selectivity - see explanation in Example 1.

B. To 10.0 g trans 3PN at 140° was added 1.0 g PFIEP[SO$_3$H]/PFIEP[CO$_2$H] (blend of perfluorinated sulfonic acid, about 70%, and perfluorinated carboxylic acid polymer, about 30%). Analysis at time intervals gave the following results:

| Time (Min) | 2PN | 4PN |
|---|---|---|
| 0 | 0 | 0.8 |
| 10 | 0 | 1.3 |
| 30 | | |
| 60 | 0 | 2.0 |

I claim:

1. A process for the preparation of 4-pentenenitrile which comprises isomerizing 3-pentenenitrile by contacting 3-pentenenitrile at a temperature in the range of about 50° to 150° C. at a pressure of 0.01 to 50 atmospheres with a heterogeneous catalyst selected from the group consisting of, acidic amorphous silica aluminates promoted with palladium in an oxidation state of at least +2 in an amount of 0.1% to 4% by weight of the catalyst, acid Y-zeolites promoted with palladium in an oxidation state of at least +2 in an amount of 0.1% to 4% by weight of the catalyst, and perfluorinated sulfonic acid ion-exchange polymers promoted with palladium or platinum in an oxidation state of at least +2.

2. The process of claim 1 in which the catalyst is perfluorinated sulfonic acid polymer containing perfluorinated carboxylic acid polymer said catalyst containing palladium or platinum in an oxidation state of at least +2.

* * * * *